US00PP27728P3

(12) United States Plant Patent
Danziger

(10) Patent No.: US PP27,728 P3
(45) Date of Patent: Feb. 28, 2017

(54) ***OSTEOSPERMUM* PLANT NAMED 'DOSTICPWHT'**

(50) Latin Name: *Osteospermum ecklonis*
Varietal Denomination: DOSTICPWHT

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 55 days.

(21) Appl. No.: 14/545,172

(22) Filed: Apr. 1, 2015

(65) Prior Publication Data

US 2016/0295785 P1 Oct. 6, 2016

(51) Int. Cl.
*A01H 5/02* (2006.01)

(52) U.S. Cl.
USPC ..... Plt./360

(58) Field of Classification Search
USPC ..... Plt./360
See application file for complete search history.

*Primary Examiner* — Anne Grunberg
(74) *Attorney, Agent, or Firm* — Cassandra Bright

(57) ABSTRACT

A new and distinct *Osteospermum* cultivar named 'DOSTICPWHT' is disclosed, characterized by a spreading growth habit, good branching, good garden performance during summer and heat tolerance. The new variety is an *Osteospermum*, normally produced as an outdoor garden or container plant.

2 Drawing Sheets

Figure 1:
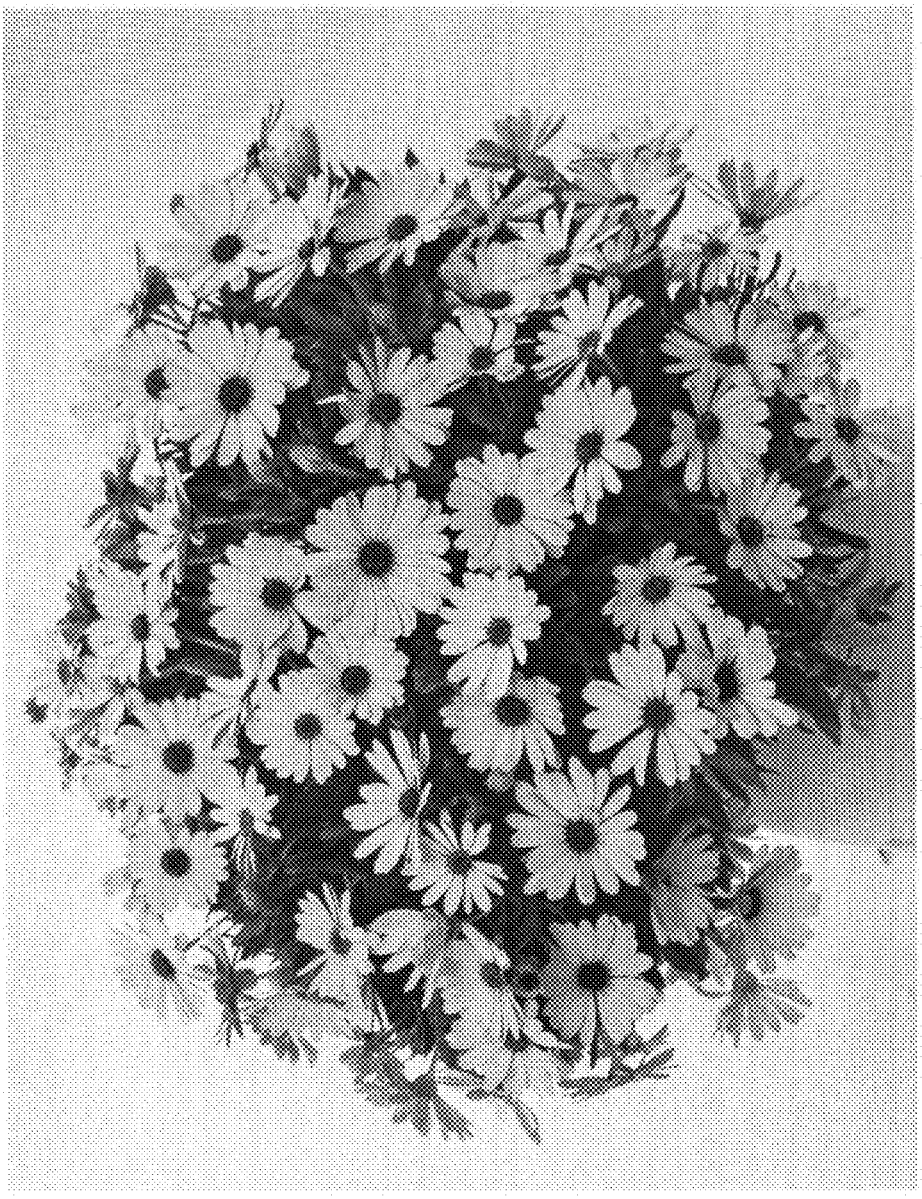

Latin name of the genus and species: *Osteospermum ecklonis*.

Variety denomination: 'DOSTICPWHT'.

BACKGROUND OF THE INVENTION

The new *Osteospermum* cultivar is a product of a planned breeding program conducted by the inventor, Gavriel Danziger, in Moshav Mishmar Hashiva, Israel. The objective of the breeding program was to produce new *Osteospermum* varieties for ornamental commercial applications. The open pollination resulting in this new variety was made during February of 2011.

The seed parent is the unpatented, proprietary variety referred to as *Osteospermum* 'OS-11-2009'. The pollen parent is unknown as it was an open pollination breeding program. The new variety was discovered in March of 2012 by the inventor in a group of seedlings resulting from the 2011 crossing, in a research greenhouse in Moshav Mishmar Hashiva, Israel.

Asexual reproduction of the new cultivar was first performed by vegetative tip cuttings. This occurred at a research greenhouse in Moshav Mishmar Hashiva, Israel in April of 2012 and has shown that the unique features of this cultivar are stable and reproduced true to type in more than 10 successive generations.

SUMMARY OF THE INVENTION

The cultivar 'DOSTICPWHT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DOSTICPWHT' These characteristics in combination distinguish 'DOSTICPWHT' as a new and distinct *Osteospermum* cultivar:

1. Heat tolerance.
2. Spreading/trailing growth habit.
3. Good garden performance during the summer.
4. Good branching.

Plants of the new cultivar 'DOSTICPWHT' are similar to plants of the seed parent, *Osteospermum* 'OS-11-2009' in most horticultural characteristics, however, plants of the new cultivar 'DOSTICPWHT' differ in the following;

1. Plant habit is more trailing.
2. More vigorous.

COMMERCIAL COMPARISON

Plants of the new cultivar 'DOSTICPWHT' are comparable to the unpatented commercial variety *Osteospermum* 'Astra White'. The two *Osteospermum* varieties are similar in most horticultural characteristics; however, the new variety 'DOSTICPWHT' differs in the following:

1. Medium size flowers. The comparator has small flowers.
2. More vigorous.
3. Trailing growth. The comparator growth is erect and compact.

Plants of the new cultivar 'DOSTICPWHT' are comparable to the commercial variety *Osteospermum* 'DOSTICWHTB', having application Ser. No. 14/545,173. The two *Osteospermum* varieties are similar in most horticultural characteristics; however, the new variety 'DOSTICPWHT' differs in the following:

1. Plants of 'DOSTICPWHT' are somewhat smaller than plants of 'DOSTICWHTB'.
2. Mature disc florets of 'DOSTICPWHT' are White and Purple, compared to Violet-Blue and White disc florets of 'DOSTICWHTB'.

3. Foliage of 'DOSTICPWHT' is on average smaller than foliage of 'DOSTICWHTB'.
4. Flowers of 'DOSTICPWHT' are on average smaller than flowers of 'DOSTICWHTB'.

BRIEF DESCRIPTION OF THE PHOTOGRAPHS

The accompanying photograph in FIG. 1 illustrates in full color a typical plant of 'DOSTICPWHT' grown outdoors, in a 13 cm pot. Age of the plant photographed is approximately 12 weeks from a rooted cutting.

Figure 2:
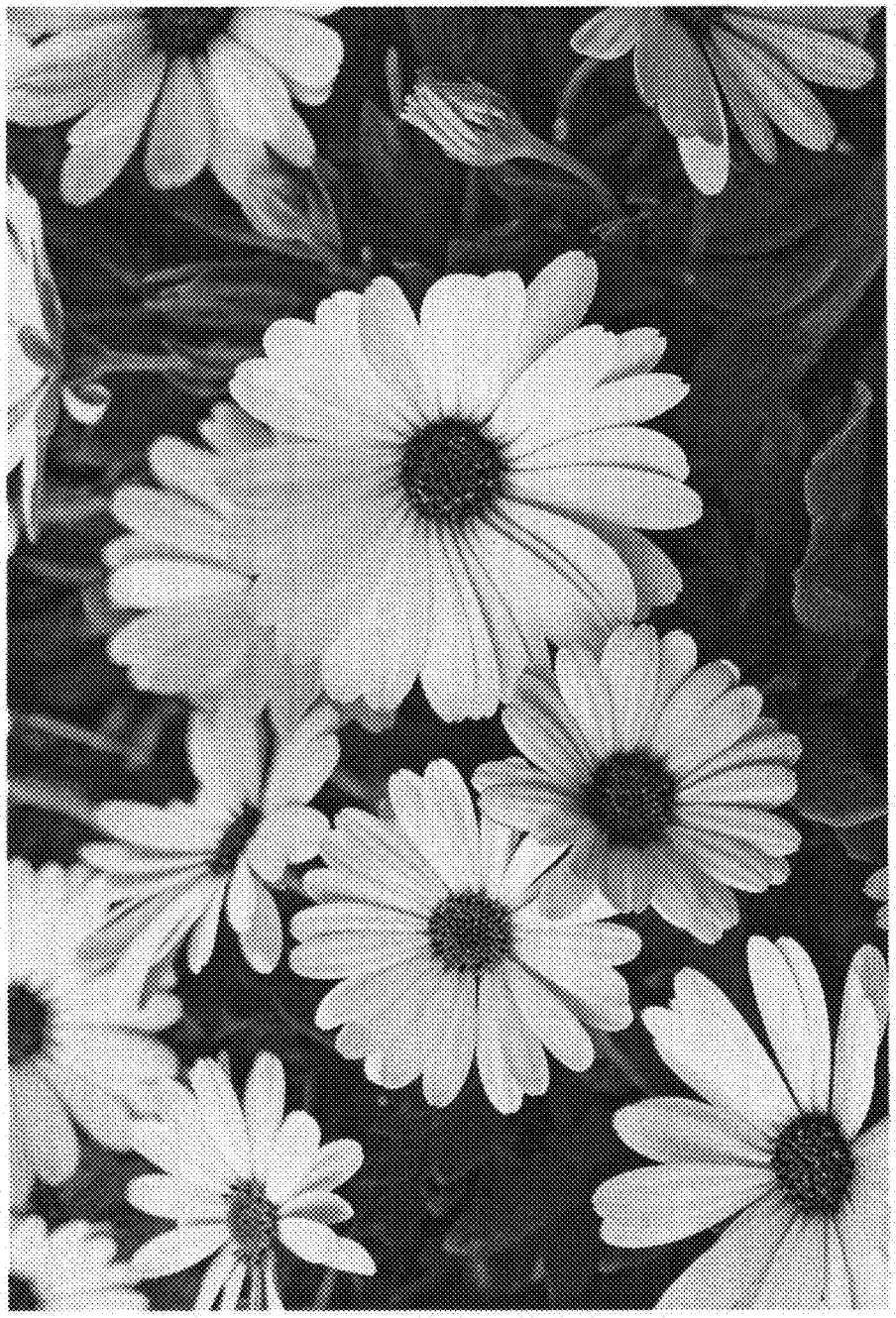

FIG. 2 illustrates a close up of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DOSTICPWHT' plants grown in the Autumn and Winter, in a greenhouse, in Moshav Mishmar Hashiva, Israel. The growing temperature ranged from 15° C. to 26° C. during the day and from 7° C. to 13° C. during the night. General light conditions are bright, normal sunlight. Measurements and numerical values represent averages of typical plant types.

Botanical classification: *Osteospermum* 'DOSTICPWHT'.

PROPAGATION

Time to rooting: 14 days at approximately 18-22° C.
Root description: Fibrous.

PLANT

Age of plant described: Approximately 100 days from a rooted cutting.
Growth habit: Spreading.
Height: Approximately 12 cm.
Plant spread: Approximately 45 cm.
Growth rate: Moderate growth rate.
Branching characteristics: Freely branching.
Length of lateral branches: Approximately 17 cm.
Diameter of lateral branches: Approximately 0.8 cm.
Texture of lateral branches: Glabrous.
Internode length: Approximately 1.0 cm.
Strength of lateral branches: Flexible.
Color of lateral branches: Near RHS Yellow-green group 144 D.
Aspect/angle of branches: 30°.
Number of leaves per lateral branch: Approximately 90.

FOLIAGE

Leaf:
- *Arrangement*.—Opposite.
- *Average length*.—Approximately 5.5 cm.
- *Average width*.—Approximately 1.5 cm.
- *Shape of blade*.—Spatulate.
- *Apex*.—Acute.
- *Base*.—Cuneate.
- *Attachment*.—Absent.
- *Margin*.—Serrate.
- *Texture of top surface*.—Glabrous, leathery.
- *Texture of bottom surface*.—Glabrous.
- *Appearance top surface*.—Shiny.
- *Appearance bottom surface*.—Matte.
- *Leaf internode length*.—Approximately 0.3 cm.
- *Color*.—Young foliage upper side: Near RHS Green 137 C. Young foliage under side: Near RHS Green 137 D. Mature foliage upper side: Near RHS Green N137 A. Mature foliage under side: Near RHS Green 137 A.
- *Venation*.—Type: Pinnate, the main vein is visible secondary veins too minute to see. Venation color upper side: Near RHS Yellow-green 144 B. Venation color under side: Near RHS Yellow-green 144 C.

Petiole: Absent.

FLOWER

Bud:
- *Bud shape*.—Oblate.
- *Bud length*.—Approximately 1 cm.
- *Bud diameter*.—Approximately 1 cm.
- *Bud color*.—Near RHS Yellow-green 146 B.

Inflorescence:
- *Form*.—Daisy-type inflorescence form with oblanceolate-shaped ray florets. Inflorescences positioned above and beyond the foliage; inflorescences terminal and axillary. Disc and ray florets developing acropetally on a capitulum. Inflorescences face mostly upright to outward.

Flower:
- *Diameter of entire flower*.—Approximately 7 cm.
- *Depth of flower*.—Approximately 0.2 cm.
- *Width of disc*.—Approximately 1.4 cm.
- *Depth of disc*.—Approximately 0.5 cm.
- *Receptacle diameter*.—1 cm.
- *Receptacle height*.—0.3 cm.

Ray florets:
- *Number of ray florets*.—Avg. 26.
- *Length*.—Approximately 3.4 cm.
- *Width*.—Approximately 1 cm.
- *Apex shape*.—Emarginate.
- *Margin*.—Entire.
- *Color*.—Ray Florets: Upper surface at first opening: Near RHS White NN155 D. Upper surface at maturity: Near RHS White NN155 C. Under surface at first opening: Near RHS Purple-violet N80 C. Under surface at maturity: Near RHS White N155A.

Disc florets:
- *Number of disc florets*.—125.
- *Length*.—Approximately 0.8 cm.
- *Width*.—Approximately 0.1 cm.
- *Shape*.—Bell shaped-campanulate.
- *Margin*.—Entire.
- *At first opening*.—Near RHS Yellow 4 D and Purple 79 A.
- *At maturity*.—Near RHS White 155 A and Purple N77 A.

Fragrance: None.

Phyllaries:
- *Number*.—Approximately 22.
- *Length*.—Approximately 0.9 cm.
- *Width*.—Approximately 0.2 cm.
- *Shape*.—Ligulate.

*Texture*.—Rough.
*Apex shape*.—Acute.
*Margin*.—Entire.
*Color*.—Near RHS Green 137 C.

Peduncle:
*Peduncle length*.—Approximately 4 cm.
*Peduncle diameter*.—Approximately 0.2 cm.
*Angle*.—Approximately 0° from center of whorl.
*Color*.—Near RHS Yellow-green 146 C.
*Peduncle texture*.—Pubescent.

REPRODUCTIVE ORGANS

Disc florets:
*Androecium*.—Stamens: Average range 100 to 120. Anther shape: Five stamens fuse to one. Anther length: Approximately 0.15 cm. Anther color: Near RHS Violet-Blue N92 A. Pollen quantity: Abundant.
*Gynoecium*.—N/A.
*Note*.—Pistils in disc flowers are degenerated and non-functional.

Ray florets:
*Androecium*.—Stamens: 26. Anther shape: Oblong. Anther length: Approximately 0.4 cm. Anther color: Near RHS Purple 79 A. Pollen quantity: Abundant.
*Gynoecium*.—Pistil number: 26. Pistil shape: Needle shape. Pistil length: Approx. 0.2 cm. Style length: Approx. 0.1 cm. Style color: Near RHS Purple 79 A. Stigma shape: Bipartite. Stigma color: Near RHS Greyed-orange 177 A. Ovary diameter: 0.1 cm. Ovary color: Near RHS Yellow 4D.

OTHER CHARACTERISTICS

Disease resistance: Neither resistance nor susceptibility to normal diseases and pests of *Osteospermum* have been observed. Typical diseases of *Osteospermum* include: *Botrytis, Pythium, Phytopthera, Rhizoctonia*. Typical pests found in *Osterspermum* include various species of Aphid, Fungus Gnats and Thrips.

Drought tolerance and cold tolerance: Good tolerance for heat, to at least 40° C. Drought tolerant.

Fruit/seed production: Seed set has been observed. Fruit is a seed-like achene.
*Shape*.—Elliptic.
*Color*.—Near RHS Brown 200 C.
*Size*.—Length: 0.6 cm. Diameter: 0.15 cm.

What is claimed is:

1. A new and distinct cultivar of *Osteospermum* plant named 'DOSTICPWHT' as herein illustrated and described.

* * * * *